United States Patent [19]

Farooq et al.

[11] 4,092,365
[45] * May 30, 1978

[54] DIPHENYL ETHER ACETALS

[75] Inventors: Saleem Farooq, Aesch; Friedrich Karrer, Basel, both of Switzerland

[73] Assignee: Ciba-Geigy Corporation, Ardsley, N.Y.

[*] Notice: The portion of the term of this patent subsequent to May 18, 1993, has been disclaimed.

[21] Appl. No.: 654,263

[22] Filed: Feb. 2, 1976

[30] Foreign Application Priority Data

Feb. 7, 1975 Switzerland .......................... 1550/75
Dec. 12, 1975 Switzerland ........................ 16152/75

[51] Int. Cl.² .............................................. C07C 43/22
[52] U.S. Cl. ............................ 260/613 R; 260/609 F; 424/337; 424/341
[58] Field of Search ..................................... 260/613 R

[56] References Cited

U.S. PATENT DOCUMENTS 2,326,702  8/1943  Taylor et al. .................... 260/613 R
3,957,885  5/1976  Karrer et al. .................... 260/613 R
3,963,786  6/1976  Karrer et al. .................... 260/613 R

*Primary Examiner*—Bernard Helfin
*Attorney, Agent, or Firm*—Harry Falber

[57] ABSTRACT

New acetals and a composition and method for combatting and controlling animal and plant pests, especially insects and in particular fruit and citrus pests. The pesticidally active acetals correspond to the formula

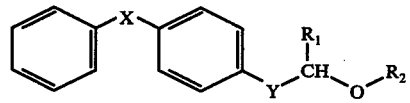

wherein
 X represents —$CH_2$—, —O— or —S—,
 Y represents —O— or —S—,
 $R_1$ represents hydrogen or $C_1$–$C_3$-alkyl, and
 $R_2$ represents $C_1$–$C_4$-alkyl, $C_1$–$C_3$-halogenoalkyl, $C_3$–$C_4$-alkenyl or $C_3$–$C_4$-alkynyl.

4 Claims, No Drawings

DIPHENYL ETHER ACETALS

The present invention relates to new acetals, to processes for producing them, and to their use in the control of pests.

The new compounds have the formula

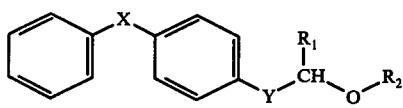

wherein
X represents —CH$_2$—, —O— or —S—,
Y represents —O— or —S—,
R$_1$ represents hydrogen or C$_1$–C$_3$-alkyl, and
R$_2$ represents C$_1$–C$_4$-alkyl, C$_1$–C$_3$-halogenoalkyl, C$_3$–C$_4$-alkenyl or C$_3$–C$_4$-alkynyl.

Compounds of the formula I are produced according to the invention by reacting, in a manner known per se, (a) a compound of the formula II with a compound of the formula III in the presence of a basically reacting compound

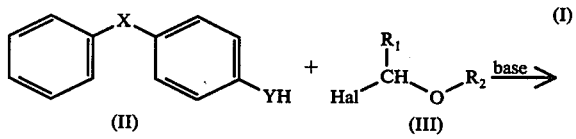

or (b) a compound of the formula II with a compound of the formula IV in the presence of an acid catalyst

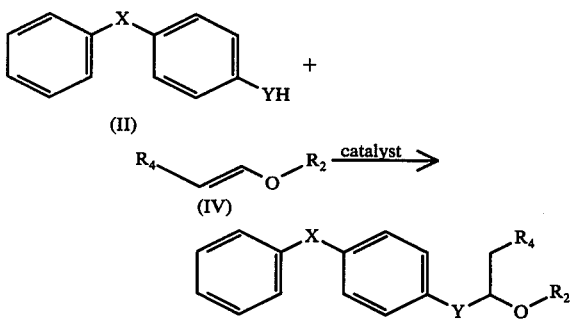

In the formulae II, III and IV, the symbols X, Y, R$_1$ and R$_2$ have the meaning previously defined, while Hal represents a halogen atom, and R$_4$ is hydrogen or C$_1$–C$_3$-alkyl. The preferred halogen is chlorine or bromine.

Suitable basically reacting compounds in the case of Process (a) are, for example:
tertiary amines such as trialkylamines, pyridine, dialkylanilines; also inorganic bases such as hydrides, hydroxides, alkoxides and carbonates of alkali metals and alkaline-earth metals.

As acid catalysts in the case of Process (b) there are advantageously used inorganic acids such as sulphuric acid or hydrochloric acid; or organic acids such as trifluoroacetic acid or p-toluenesulphonic acid.

The Processes (a) and (b) described above are performed generally at a temperature of about −15° to 130° C, preferably 20° to 100° C, under normal pressure and in the presence of inert solvents and/or diluents.

Suitable solvents and/or diluents are, for example, ethers such as diethyl ether, diisopropyl ether, 1,2-dimethoxyethane, dioxane or tetrahydrofuran, hydrocarbons such as benzene, toluene, xylene or ethylbenzene, ketones such as acetone, methyl ethyl ketone or cyclohexanone, or others such as dimethylformamide, dimethylsulphoxide or hexamethylphosphoric acid amide.

The starting materials of the formulae II, III and IV are known compounds, or they can be produced by processes known per se, which are described in the literature (see, e.g., J. Chem. Soc. 1974, 6, pp. 700–704).

Preferred compounds of the formula I according to the invention are those wherein X, Y and R$_1$ have the meanings already defined, and R$_2$ stands for

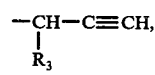

wherein R$_3$ represents hydrogen or methyl.

Also to be emphasized with regard to their effectiveness are the compounds of the formula I wherein
X represents —O— or —S—,
Y represents —O— or —S—,
R$_1$ represents hydrogen or C$_1$–C$_3$-alkyl, and
R$_2$ represents —CH$_2$—C≡CH.

Particularly preferred among these compounds are those wherein Y stands for —O—.

The compounds of the formula I are suitable for the control of various animal and plant pests; they are particularly suitable for the control and influencing of the development of insects, as well as of members of the order acarina of the families:
Ixodidae, Argasidae, Tetranychidae, Dermanyssidae; as well as of insects of the families: Acrididae, Blattidae, Gryllidae, Gryllotalpidae, Tettigoniidae, Cimicidae, Pyrrhocoridae, Reduviidae, Aphididae, Delphacidae, Diaphididae, Pseudococcidae, Chrysomilidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae or Pulicidae.

The compounds of the formula I are especially valuable for the control of fruit and citrus pests.

The insecticidal action can be substantially broadened and adapted to suit given circumstances by the addition of other insecticides and/or acaricides. Suitable additives are, for example:
organic phosphorus compounds,
nitrophenols and derivatives,
formamidines, ureas, carbamates,
chrysanthemum acid derivatives or
chlorinated hydrocarbons.

The compounds of formula I can be used on their own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are prepared in a manner known per se by the intimate mixing and/or grinding of active substances of formula I with suitable carriers, optionally with the addition of dispersing agents or solvents which are inert to the active substances. The active substances can be prepared and used in the following formulations:

solid preparations:
dusts, scattering agents or granulates (coated granulates, impregnated granulates and homogeneous granulates);
liquid preparations:
(a) water-dispersible active-substance concentrates: wettable powders, pastes and emulsions;
(b) solutions.

The content of active substance in the described compositions is between 0.1 and 95%.

The active substances of formula I can be formulated, for example, as follows:

Dusts

The following substances are used in the preparation of (a) a 5% dust, and (b) a 2% dust:

(a)
5 parts of Active Substance,
95 parts of talcum;

(b)
2 parts of Active Substance,
1 part of highly dispersed silicic acid,
97 parts of talcum.

The active substances are mixed and ground with the carriers.

Granulate

The following substances are used to produce a 5% granulate:
5 parts of Active Substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin, and the mixture is dissolved with 6 parts of acetone; the polyethylene glycol and cetyl polyglycol ether are then added. The solution obtained is sprayed on to kaolin, and the acetone is substantially evaporated off.

Wettable powders

The following constituents are used to prepare (a) a 40%, (b) and (c) a 25%, and (d) a 10% wettable powder:

(a)
40 parts of Active Substance,
5 parts of sodium lignin sulphonate,
1 part of sodium dibutyl-naphthalene sulphonate,
54 parts of silicic acid;

(b)
25 parts of Active Substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)
25 parts of Active Substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)
10 parts of Active Substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, and the mixture is then ground in the appropriate mills and rollers. Wettable powders are obtained which can be diluted with water to give suspensions of any desired concentration.

Emulsifiable concentrates

The following substances are used to produce (a) a 10%, (b) a 25% and (c) a 50% emulsifiable concentrate:

(a)
10 parts of Active Substance,
3.4 parts of epoxidised vegetable oil,
3.4 parts of a combination emulsifier consisting of fatty alcohol polyglycol ether and alkylaryl sulphonate calcium salt,
40 parts of dimethylformamide,
43.2 parts of xylene;

(b)
25 parts of Active Substance,
2.5 parts of epoxidised vegetable oil,
10 parts of an alkylarlysulphonate/fatty alcohol polyglycol ether mixture,
5 parts of dimethylformamide,
57.5 parts of xylene;

(c)
50 parts of Active Substance,
4.2 parts of tributylphenol-polyglycol ether,
5.8 parts of calcium-dodecylbenzene sulphonate,
20 parts of cyclohexanone,
20 parts of xylene.

It is possible to produce from these concentrates, by dilution with water, emulsions of any desired concentration.

Sprays

The following constituents are used to prepare (a) a 5% spray, and (b) a 95% spray:

(a)
5 parts of Active Substance,
1 part of epichlorohydrin,
94 parts of ligroin (boiling limits 160°–190° C);

(b)

95 parts of Active Substance,
5 parts of epichlorohydrin.

EXAMPLE 1

Production of propargyloxy-[4-(phenylmercapto)-phenoxy]-methane:

10.4 g (0.075 mole) of finely pulverised anhydrous potassium carbonate is added to a solution of 15.2 g (0.075 mole) of 4-hydroxydiphenylsulphide in 80 ml of anhydrous acetone, and the mixture is boiled for 45 minutes. There is then added dropwise, in the course of 10 minutes, 7.1 g (0.0675 mole) of propargyloxy-chloromethane, and boiling is continued for a further 5 hours at reflux temperature. In further processing, the reaction solution is filtered off from the solid deposit, and the filtrate is freed in vacuo from the solvent. The residue is dissolved in ether; the solution is washed three times with 10% potassium hydroxide solution, and subsequently four times with saturated sodium chloride solution. After drying of the ether phase over sodium sulphate, the solvent is distilled off in vacuo, and the residue is dried in high vacuum. There is obtained propargyloxy-[4-(phenylmercapto)-phenoxy]-methane in the form of colourless oil having a refractive index of $n_D^{20} = 1.5975$.

EXAMPLE 2

Production of 1-(2-chloroethoxy)-1-[(4-phenoxy)-phenoxy]-ethane:

64 g of freshly distilled 2-chloroethyl-vinyl ether is placed into a flask; one drop of concentrated hydrochloric acid is added, and thereupon an addition is made in portions at room temperature, with stirring, of 93 g of 4-phenoxy-phenol (duration of addition about 1 hour). During the addition of 4-phenoxy-phenol, the temperature rises to about 32°–34° C, with the 4-phenoxy-phenol completely dissolving. After two further hours' stirring, the reaction mixture is diluted with 300 ml of diethyl ether; the ether solution is washed three times with 10% potassium hydroxide solution and three times with saturated sodium chloride solution. The ether solution is subsequently dried over sodium sulphate, and the ether and the readily volatile constituents (traces of 2-chloroethyl-vinyl ether) are completely removed in vacuo. There is obtained 1-(2-chloroethoxy)-1-[(4-phenoxy)-phenoxy]-ethane in the form of colorless oil having a refractive index of $n_D^{20} = 1.5516$ (yield 98%).

EXAMPLE 3

The following compounds of the formula I are produced in a manner analogous to that of Examples 1 and 2:

| X | Y | R$_1$ | R$_2$ | $n_D^{20}$ |
|---|---|---|---|---|
| S | O | H | —CH$_2$—C≡CH | 1,5975 |
| S | O | CH$_3$ | —CH$_2$—C≡CH | 1,5940 |
| S | S | H | —CH$_2$—C≡CH | 1,6346 |
| S | S | H | —CH$_2$—CH=CH$_2$ | 1,5218 |
| CH$_2$ | O | H | —CH$_2$—C≡CH | 1,5626 |
| O | O | H | —CH$_2$—C≡CH | 1,5640 |
| O | O | H | —CH(CH$_3$)$_2$ | 1,5368 |
| O | O | C$_2$H$_5$ | —C$_2$H$_5$ | 1,5358 |
| O | O | CH$_3$ | —C$_2$H$_5$ | 1,5419 |
| O | O | CH$_3$ | i-C$_4$H$_9$ | 1,5262 |
| O | O | CH$_3$ | —CH$_2$—CH$_2$—Cl | 1,5516 |
| O | O | H | CH$_3$<br>|<br>—CH—C≡CH | 1,5510 |
| O | O | CH$_3$ | CH$_3$<br>|<br>—CH—C≡CH | 1,5496 |
| S | O | H | CH$_3$<br>|<br>—CH—C≡CH | 1,5891 |
| S | O | CH$_3$ | CH$_3$<br>|<br>—CH—C≡CH | 1,5842 |
| CH$_2$ | O | H | CH$_3$<br>|<br>—CH—C≡CH | 1,5491 |
| CH$_2$ | O | CH$_3$ | i-C$_4$H$_9$ | 1,5210 |
| CH$_2$ | O | CH$_3$ | —CH$_2$—CH$_2$—Cl | 1,5636 |
| CH$_2$ | O | CH$_3$ | C$_2$H$_5$ | 1,5411 |
| CH$_2$ | O | H | i-C$_4$H$_9$ | 1,5360 |
| CH$_2$ | O | CH$_3$ | —CH$_2$—C≡CH | 1,5531 |
| O | O | CH$_3$ | —CH$_2$—C≡CH | |
| CH$_2$ | O | C$_2$H$_5$ | —CH$_2$—C≡CH | 1,5323 |
| O | O | C$_2$H$_5$ | —CH$_2$—C≡CH | 1,5237 |
| S | O | C$_2$H$_5$ | —CH$_2$—C≡CH | |
| CH$_2$ | O | i-C$_3$H$_7$ | —CH$_2$—C≡CH | 1,5210 |
| O | O | i-C$_3$H$_7$ | —CH$_2$—C≡CH | 1,5092 |
| S | O | i-C$_3$H$_7$ | —CH$_2$—C≡CH | |
| CH$_2$ | O | n-C$_3$H$_7$ | —CH$_2$—C≡CH | |
| O | O | n-C$_3$H$_7$ | —CH$_2$—C≡CH | |
| S | O | n-C$_3$H$_7$ | —CH$_2$—C≡CH | |

EXAMPLE 4

(A) Contact action on *Dysdercus-fasciatus* larvae

A specific amount of a 0.1% acetonic active-substance solution (corresponding to 10 mg of active substance per square meter) was transferred by pipet to an aluminum dish and uniformly distributed. After evaporation of the acetone, 10 larvae in the 5th stage of *Dysdercus fasciatus* were placed into the treated dish containing feed and moist cotton wool. The dish was then covered with a perforated lid. After about 10 days, i.e., as soon as the control insects had moulted into adults, the test insects were examined to determine the number of normal adults.

Compounds according to Examples 1–3 exhibited a good action in the above test.

(B) Contact action on *Aedes-aegypti* larvae

About 20 2-day-old larvae of the yellow-fever mosquito (*Aedes aegypti*) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

Compounds according to Examples 1–3 exhibited a good action in the above test.

(C) Contact action on *Tenebrio-molitor* pupae

A specific amount of a 0.1% acetonic active-substance solution corresponding to 10 mg of active substance per square meter was transferred by pipet into an aluminum dish and uniformly distributed. After evaporation of the acetone, 10 freshly formed pupae were placed onto the treated surface, and the dish was covered with a perforated lid. After the control insects had left the cocoon as imagines, the test insects were examined to determine the number of normal adults.

Compounds according to Examples 1–3 exhibited a good action in the above test.

EXAMPLE 5

Action against *Ephestia kuhniella*

50 g of wheat flour was mixed in two beakers with a specific amount of active substance, formulated as a 5% dust, so that concentration was 0.05%. Into each beaker (25 g of flour) there were placed 10 larvae of *Ephesta kuhniella*. The pattern of population was ascertained over a period of 8 weeks and the number of moths was determined.

Compounds according to Examples 1-3 exhibited a good action in this test against *Ephestia kuhniella*.

EXAMPLE 6

Action against red spider mites

*Phaseolus vulgaris* (bush beans) were infested, 12 hours before the test for acaricidal action, with an infested piece of leaf from a mass culture of *Tetranychus urticae*. The transferred mobile stages were sprayed with the emulsified test preparations, at a concentration of 0.04%, by means of a chromatography-sprayer in a manner ensuring no running-off of the spray liquor. An assessment was made after 2 to 7 days, by examination under a binocular, of the living and of the dead larvae, adults and eggs, and the results were expressed in percentages. The treated plants were kept during the holding time in greenhouse compartments at 25° C.

Compounds according to Examples 1-3 exhibited in the above test a good action against eggs, larvae and adults of *Tetranychus urticae*.

We claim:

1. A compound of the formula I

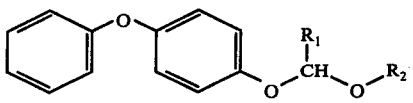

wherein
 $R_1$ represents hydrogen or $C_1$-$C_3$-alkyl, and
 $R_2$ represents $C_1$-$C_4$-alkyl, $C_1$-$C_3$-halogenoalkyl, $C_3$-$C_4$-alkenyl or $C_3$-$C_4$-alkynyl.

2. The compound according to claim 1 wherein $R_2$ represents

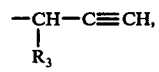

whereby
 $R_3$ stands for hydrogen or methyl.

3. The compound according to claim 2, wherein $R_2$ represents —$CH_2$—$C\equiv H$.

4. The compound according to claim 3 having the formula

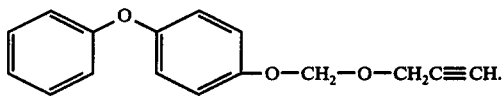

* * * * *